(12) United States Patent
Kukita et al.

(10) Patent No.: US 9,164,063 B2
(45) Date of Patent: Oct. 20, 2015

(54) SENSING DEVICE, SENSING SYSTEM, AND SENSING METHOD

(75) Inventors: Hiroyuki Kukita, Saitama (JP); Shunichi Wakamatsu, Saitama (JP); Wakako Shinobu, Saitama (JP)

(73) Assignee: NIHON DEMPA KOGYO CO., LTD., Tokyo (JP)

( * ) Notice: Subject to any disclaimer, the term of this patent is extended or adjusted under 35 U.S.C. 154(b) by 394 days.

(21) Appl. No.: 13/586,879

(22) Filed: Aug. 16, 2012

(65) Prior Publication Data
US 2013/0042672 A1 Feb. 21, 2013

(30) Foreign Application Priority Data
Aug. 19, 2011 (JP) ................... 2011-179529

(51) Int. Cl.
*G01N 29/00* (2006.01)
*G01N 29/036* (2006.01)
*G01N 15/06* (2006.01)

(52) U.S. Cl.
CPC .............. *G01N 29/036* (2013.01); *G01N 15/06* (2013.01); *G01N 2291/0256* (2013.01)

(58) Field of Classification Search
CPC ... H03B 5/1203; H01L 27/1214; A61B 8/461
USPC ........................................... 73/579
See application file for complete search history.

(56) References Cited

U.S. PATENT DOCUMENTS

| 2004/0187580 | A1* | 9/2004 | Nozaki ............................ 73/580 |
| 2009/0128118 | A1 | 5/2009 | Ito |
| 2009/0308142 | A1* | 12/2009 | Onishi et al. ...................... 73/73 |

FOREIGN PATENT DOCUMENTS

| EP | 0823777 B1 * | 3/2003 |
| JP | 2006-258787 | 9/2006 |
| JP | 2006-287765 | 10/2006 |
| JP | 2007-124213 | 5/2007 |
| JP | 2008-185451 | 8/2008 |
| JP | 2011-022141 | 2/2011 |

OTHER PUBLICATIONS

"Office Action of Japan Counterpart Application", issued on Feb. 24, 2015, p. 1-p. 2, in which two of the listed references (JP2011-022141A and JP2007-124213A) were cited.

* cited by examiner

*Primary Examiner* — Hezron E Williams
*Assistant Examiner* — Tarun Sinha
(74) *Attorney, Agent, or Firm* — Jianq Chyun IP Office

(57) ABSTRACT

A sensing device is to be connected to a piezoelectric resonator for sensing a target substance in a sample fluid based on oscillation frequency of the piezoelectric resonator. The sensing device includes an oscillator circuit, a voltage supply unit, an information obtaining unit, and a voltage adjusting unit. The oscillator circuit is commonalized for a plurality kinds of piezoelectric resonators. The voltage supply unit is configured to supply a DC drive voltage to the oscillator circuit. The information obtaining unit is configured to obtain type information of a piezoelectric resonator which is connected to the oscillator circuit. The voltage adjusting unit is configured to adjust the DC drive voltage to a voltage corresponding to the connected piezoelectric resonator based on the type information obtained by the information obtaining unit.

6 Claims, 6 Drawing Sheets

SENSING DEVICE, SENSING SYSTEM, AND SENSING METHOD

CROSS-REFERENCE TO RELATED APPLICATIONS

This application claims the priority benefit of Japan application serial no. 2011-179529, filed on Aug. 19, 2011. The entirety of the above-mentioned patent application is hereby incorporated by reference herein and made a part of this specification.

FIELD

This disclosure pertains to, inter alia, sensing devices and sensing methods that measure a concentration or the like of a target substance in a sample fluid using change in frequency of a piezoelectric resonator. This change is caused by, for example, an absorption of the target substance by an adsorbing layer on the piezoelectric resonator.

DESCRIPTION OF THE RELATED ART

A known sensing method uses a sensing device that includes a quartz sensor as a method for sensing a target substance in a sample fluid such as a trace amount of protein in blood or serum. On electrodes of a crystal unit that is used in the sensing device, an adsorbing layer is formed to capture antigens using an antigen-antibody reaction. Then, the antigens are captured by the adsorbing layer. Variation in oscillation frequency of the crystal unit is estimated as an amount of captured antigens, that is, concentration of the target substance in a sample solution. The sensing device employs an analog Colpitts oscillator circuit as a preferred circuit so as to ensure stabilized frequency of the quartz sensor.

Quartz sensors used for the sensing device may have mutually different CI values (crystal impedance values) for respective types of the quartz sensors though crystal units with the same frequency are used. The reason is that crystal elements and electrodes have mutually different shapes. In order to ensure stable oscillation of the oscillator circuit in a liquid phase, for example, an oscillation margin that is three times as large as a CI value of the crystal unit is desired. In the case where a CI value of the crystal unit is relatively too low compared with an equivalent series resistance of the oscillator circuit, problems occur in initial stability, frequency drift, a temperature characteristic and the like of oscillation. In the case where the CI value is relatively too high, the oscillation margin becomes low. This destabilizes oscillation in a solution, especially in a solution with high viscosity.

Accordingly, the analog Colpitts oscillator circuit needs an oscillator circuit that is designed according to a characteristic of the quartz sensor. Thus, a dedicated oscillator circuit corresponding to a type of the quartz sensor is required. As a result, this causes a need for designing a new oscillator circuit every time a new quartz sensor is developed thanks to an improvement of a characteristic and a performance of the quartz sensor.

Japanese Patent Publication No. 2008-185451 discloses a configuration that adjusts a supply voltage so as to improve measurement accuracy of a Q-value of a crystal unit. Japanese Patent Publication No. 2006-287765 discloses a technique where an oscillator circuit has an inverter with a variable size. This allows a setting from outside to control the size of the inverter, thus ensuring an oscillation margin. However, both the above mentioned references do not disclose a configuration that allows quartz sensors with different CI values, which is a problem in this disclosure, to be used with a common oscillator circuit.

Thus, a need exists for a sensing device and a sensing method that is not susceptible to the drawback mentioned above.

SUMMARY

An aspect of this disclosure is directed to a sensing device to be connected to a piezoelectric resonator for sensing a target substance in a sample fluid based on oscillation frequency of the piezoelectric resonator. The piezoelectric resonator includes a piezoelectric piece, an electrode disposed on the piezoelectric piece, and an adsorbing layer located on the electrode. The adsorbing layer adsorbs a target substance in the sample fluid. The piezoelectric resonator is configured to change a natural frequency of the piezoelectric resonator by adsorbing the target substance. The sensing device includes an oscillator circuit, a voltage supply unit, an information obtaining unit, and a voltage adjusting unit. The oscillator circuit is commonalized for a plurality kinds of piezoelectric resonators. The voltage supply unit is configured to supply a DC drive voltage to the oscillator circuit. The information obtaining unit is configured to obtain a type information of the piezoelectric resonator which is connected to the oscillator circuit. The voltage adjusting unit is configured to adjust the DC drive voltage to a voltage corresponding to the connected piezoelectric resonator based on the type information obtained by the information obtaining unit.

BRIEF DESCRIPTION OF THE DRAWINGS

The foregoing and additional features and characteristics of this disclosure will become more apparent from the following detailed description considered with the reference to the accompanying drawings, wherein.

DETAILED DESCRIPTION

First Embodiment

Figure 1:
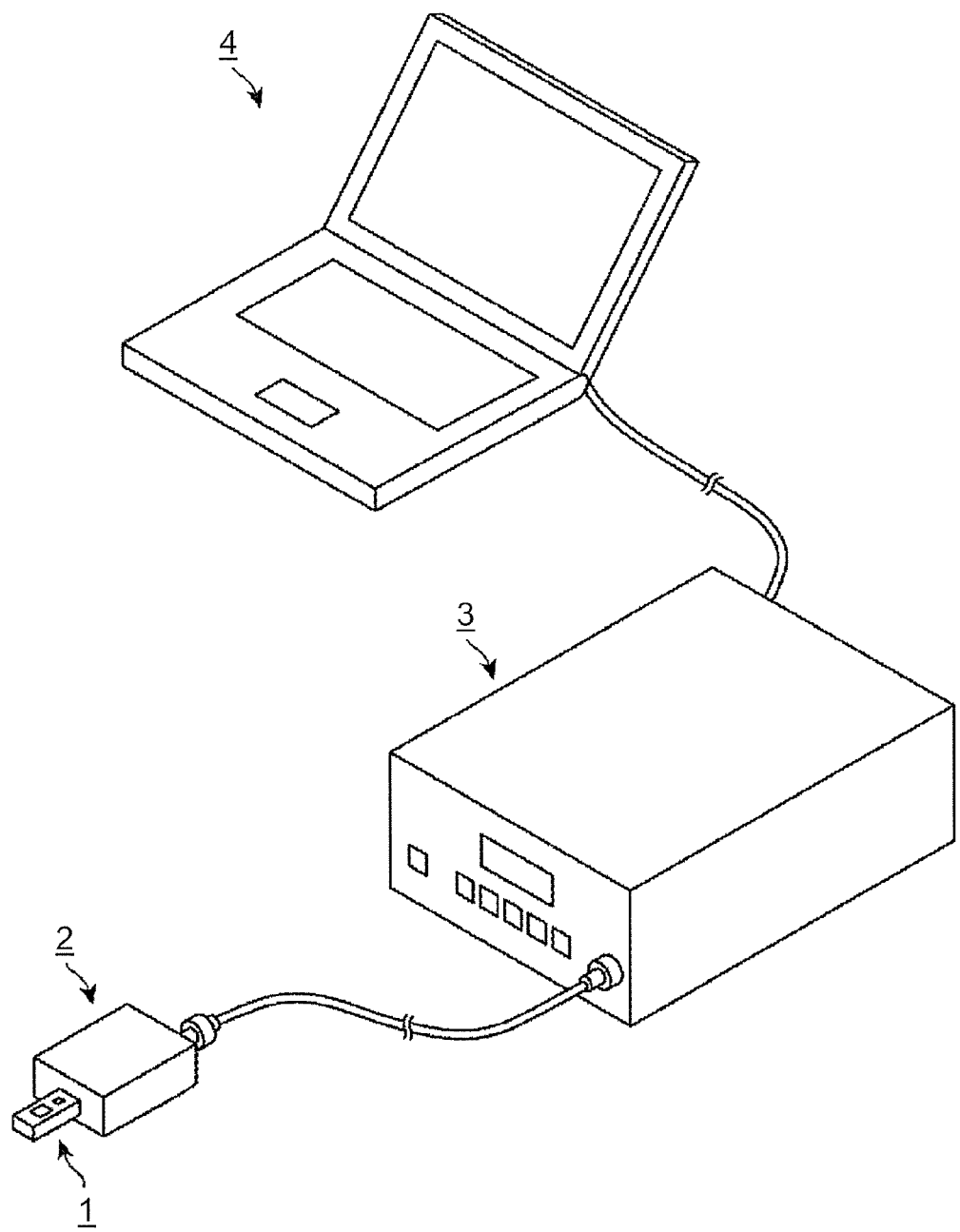
FIG. 1 is a perspective view illustrating a whole sensing device according to a first embodiment disclosed here.

A sensing device with a piezoelectric sensor employs various systems such as a system that accumulates a sample solution and a system that flows a sample solution. In this embodiment, a sensing device that accumulates a sample solution to perform measurement will be described. As illustrated in FIG. 1, the sensing device includes a quartz sensor 1, an oscillator circuit unit 2, a main body 3, and a user interface 4. The quartz sensor 1 is a kind of piezoelectric sensors to which sample solutions containing a target substance are supplied. The oscillator circuit unit 2 is removably connected to the quartz sensor 1. The main body 3 is connected to the oscillator circuit unit 2. The user interface 4 is connected to the main body 3, and includes a personal computer that functions to set parameters in a frequency measuring unit 30 and to display frequency information.

Figure 2A:
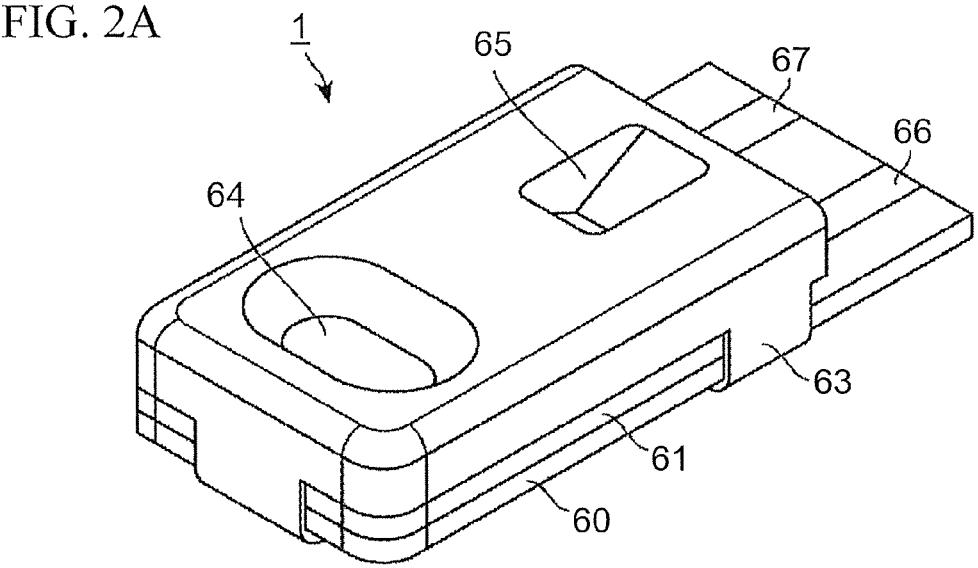
FIG. 2A is a perspective view illustrating a quartz sensor according to the embodiment disclosed here.
Figure 2B:
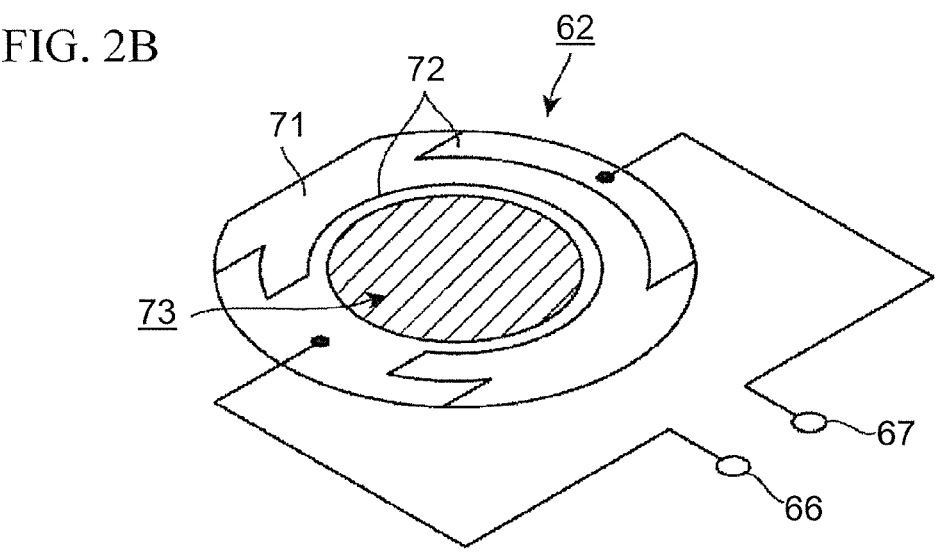
FIG. 2B is a perspective view illustrating a crystal unit that is used for the quartz sensor according to the embodiment disclosed here.

FIG. 2A illustrates an appearance of the quartz sensor 1. FIG. 2B illustrates wiring of a crystal unit in the quartz sensor 1. The quartz sensor 1 is constituted as follows. A rubber sheet 61 is stacked on a printed circuit board 60, which is a wiring board. A crystal unit 62 corresponding to a piezoelectric resonator is disposed on the top of the rubber sheet 61. An upper cover case 63 is mounted on the crystal unit 62. The crystal unit 62 includes excitation electrodes 72 (excitation electrode 72 at back surface side is not illustrated in FIG. 2B) on both surfaces of a blank 71, which is in a circular shape, for example. The respective electrodes 72 are electrically connected to printed wirings 66 and 67 on the printed circuit board 60 with conductive epoxy or the like. In contrast, an adsorbing layer 73 to adsorb the target substance is formed at a front surface side of the electrode 72. The adsorbing layer 73 includes, for example, an antibody to capture antigens, which are the target substances, in the sample solution using antigen-antibody reaction. The upper cover case 63 includes an injection port 64 of the sample solution and an observation port 65.

The quartz sensor 1 is removed by pulling out the printed circuit board 60 from the oscillator circuit unit 2 as described above. By inserting the quartz sensor 1, the crystal unit 62 is electrically connected to an oscillator circuit 20 of the oscillator circuit unit 2 via the printed wirings 66 and 67. The quartz sensor 1 is used as follows: Injecting the sample solution containing the target substance into the quartz sensor 1 from the injection port 64, the adsorbing layer 73 is caused to selectively react with the target substance if the sample solution includes the target substance. This consequently changes oscillation frequency of the crystal unit 62 by a mass load effect.

Figure 3:
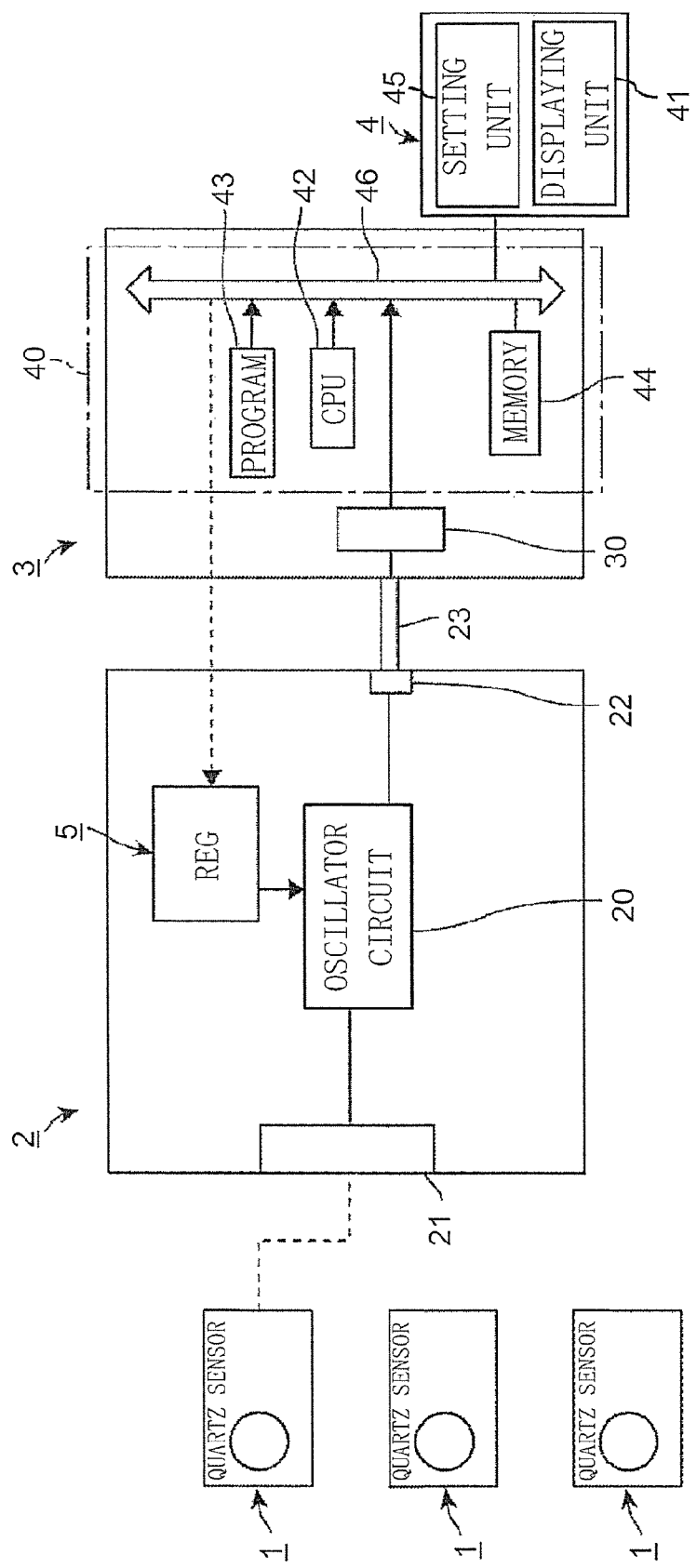
FIG. 3 is an explanatory block diagram illustrating a whole circuit of the sensing device according to the embodiment disclosed here.

The oscillator circuit unit 2 includes the oscillator circuit 20, a connecting terminal 21, a connecting terminal 22, and a regulator 5 as illustrated in FIG. 3. The oscillator circuit 20 includes an analog Colpitts oscillator circuit. The connecting terminal 21 is a terminal of the preceding stage that connects each of the crystal units 62 of the quartz sensors 1 to the oscillator circuit 20. The connecting terminal 21 is commonalized for the plurality kinds of the quartz sensors 1. The connecting terminal 22 is a terminal of the succeeding stage that connects the oscillator circuit 20 to the frequency measuring unit 30 of the main body 3, which is described later, via a cable 23. The regulator 5 corresponds to a voltage supply unit that supplies a driving DC voltage to the oscillator circuit 20.

Figure 4:
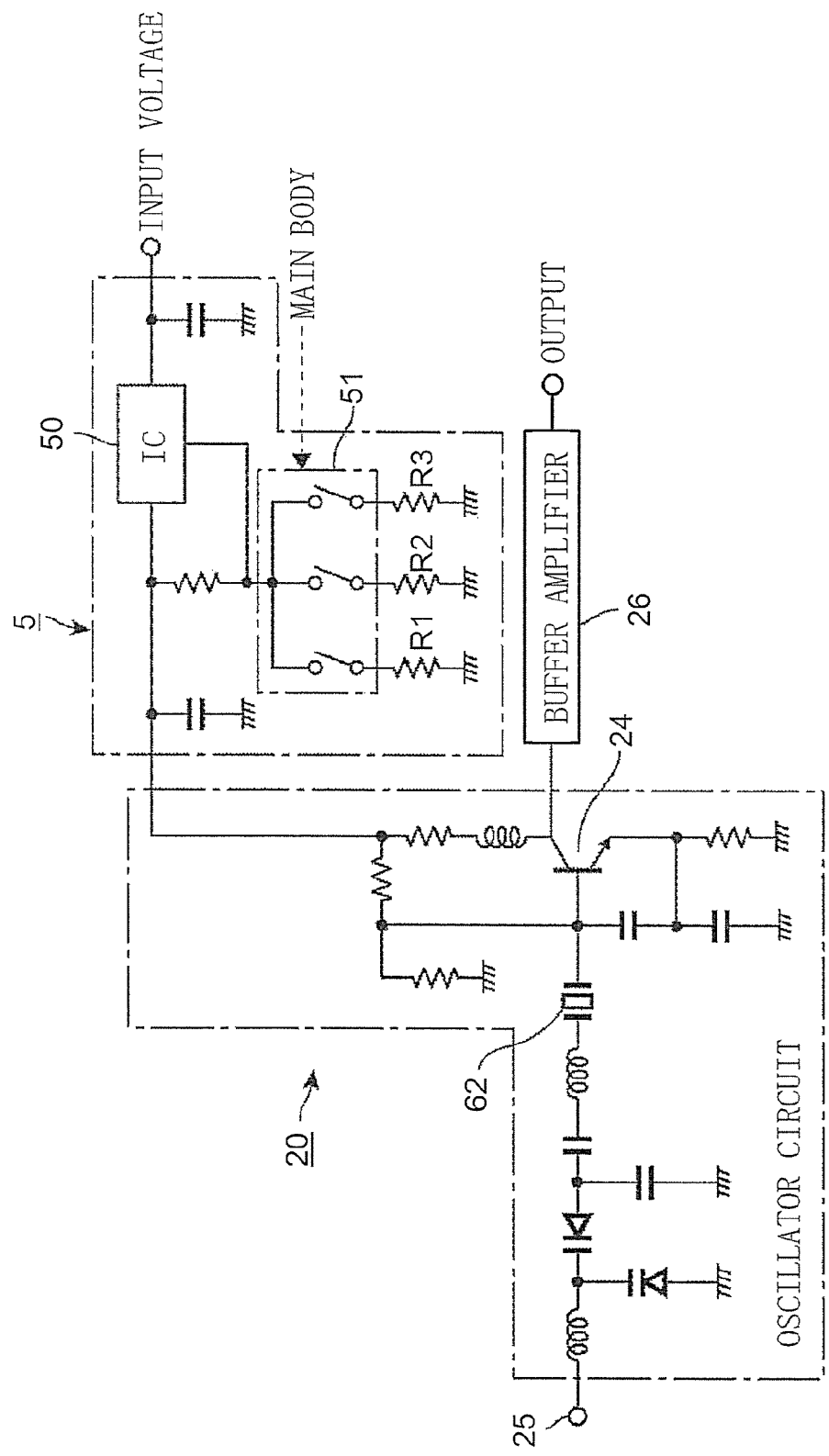
FIG. 4 is an explanatory circuit diagram illustrating an oscillator circuit of the sensing device and a circuit of a voltage supply unit according to the embodiment disclosed here.

The oscillator circuit (the analog Colpitts oscillator circuit) 20 includes a transistor 24 as an amplifier, split capacitors C1 and C2, and the like as illustrated in FIG. 4. The regulator 5, which is a voltage supply unit, supplies a driving DC voltage to the transistor 24. The oscillator circuit 20 includes a terminal 25, which supplies a control voltage to control oscillation frequency, and a buffer amplifier 26. Connecting the quartz sensor 1 to the connecting terminal 21 of the oscillator circuit unit 2 allows the crystal unit 62 to function as a part of the oscillator circuit.

As illustrated in FIG. 4, the regulator 5 includes a regulator IC (an integrated circuit). The regulator 5 includes a variable resistance portion for voltage adjustment between an output terminal of an IC 50 and ground. The variable resistance portion includes, for example, three resistors R1 to R3, which have mutually different resistance values, and a switch 51, which switches and selects the resistors R1 to R3. The switch 51 is selected based on a control signal from the main body 3, thus a resistor is selected corresponding to the control signal.

Returning to FIG. 3, the main body 3 includes a frequency measuring unit 30 and a controller 40. The frequency measuring unit 30 is connected to the oscillator circuit 20 via the connecting terminal 22 and the cable 23. The controller 40 has functions such as a function that performs data processing on frequency measured by the frequency measuring unit 30 and a function that supplies the control signal for voltage adjustment to the regulator 5 of the oscillator circuit unit 2. The frequency measuring unit 30 may employ a frequency counter. The frequency measuring unit 30 may also measure frequency with a digital processing technique using a rotational vector, which is disclosed and proposed by this applicant in Japanese Patent Publication No. 2006-258787.

The controller 40 includes a computer with a bus 46, which is illustrated in the drawing. The bus 46 is connected to a CPU 42, which performs various arithmetic operations, a memory 44, which stores a setting value of the voltage of the regulator 5 corresponding to type information, and a program 43. The program 43 includes a group of steps to read out the setting value of the voltage corresponding to the type information of the quartz sensor (the crystal unit) that is input from the user interface 4 constituted of a personal computer, thus setting the output voltage of the regulator 5. The program 43 is stored in a program storage, which is not illustrated in FIG. 3.

The memory 44 includes an area that stores time-series data of oscillation frequency, which is measured by the frequency measuring unit 30, and an area that stores voltage data. The voltage data associates the type information of the quartz sensor with the driving voltage (the supply voltage) of the oscillator circuit 20. Before description of the voltage data, the user interface 4 will be described. The user interface 4 includes, for example, a function to display frequency data, which is stored in the memory 44 of the main body 3, on a displaying unit 41, and an input unit 45, (setting unit 45 shown in FIG. 3) that receives the type information of the quartz sensor to the memory 44.

Next, the voltage data will be described. Quartz sensors used for the sensing device have different sizes of electrodes in the crystal unit depending on their usage, thus having different CI values even in the case where the respective quartz sensors have the same frequency. As described above, in the case where oscillation is performed in a liquid phase, the negative resistance of the oscillator circuit 20 is recommended to employ a circuit with a negative resistance three times as large as the CI value of the crystal unit. For example, in the case where the quartz sensors with CI values in pure water of 150Ω and 450Ω are used for oscillation, oscillator circuits with the respective negative resistances of 450Ω and 1350Ω are preferred to be prepared.

Here, the inventors found that adjusting drive power of the analog Colpitts oscillator circuit is able to change the negative resistance. Accordingly, a drive voltage value for an appropriate negative resistance corresponding to a CI value (a CI value of the crystal unit in the liquid phase) of the quartz sensor 1 is preliminarily obtained for each type of the quartz sensors 1 to be used for the sensing device. Data (voltage data) that associate the types of the quartz sensor and drive voltage information for setting the drive voltage values, are stored in the memory 44. In the description of this embodiment, the three kinds of quartz sensors 1 are assumed. The output voltage of the regulator 5 is adjusted with the switch 51 by selecting one of the resistors R1 to R3. That is, the drive voltage information corresponds to data for outputting a switching signal. The data is indicative of an opening and closing state of the switch 51, which is used for selecting the respective resistors R1 to R3 so as to obtain an appropriate voltage value corresponding to each of the three kinds of quartz sensors 1. Therefore, the CPU 42 of the controller 40 outputs the switching signal from the memory 44 to the switch 51, thus driving the oscillator circuit 20 with the corresponding drive voltage. The program 43 of the controller 40 includes a group of steps to perform a sequence of operations for setting the drive voltage. In this embodiment, the program 43, the memory 44, the switch 51, and the resistors R1 to R3 correspond to a voltage adjusting unit that adjust the driving DC voltage supplied to the oscillator circuit 20. The resistors R1 to R3 also function as a part of a voltage supply unit.

Next, the effects of this embodiment will be described. Now, assume that, for example, a target substance is sensed using the quartz sensor 1 with a CI value of 200Ω in the liquid phase as illustrated in FIG. 3. First, an operator inputs type information of a quartz sensor 1 through the user interface 4. The CPU 42 of the controller 40 reads out drive voltage information from the voltage data of the memory 44 based on the input type information, and then selects a resistor (for example, R1) for voltage adjustment of the regulator 5 through the switch 51. In view of this, the regulator 5 sets a voltage value of the supply voltage (the drive voltage), which is supplied to the oscillator circuit 20, to a predetermined value for the quartz sensor 1, thus adjusting the negative resistance to a value nearly three times as large as the CI value in the liquid phase of the crystal unit of the quartz sensor 1. This results in the oscillation margin of the oscillator circuit that is nearly three times as large as the CI value of the quartz sensor 1, thus ensuring stabilized oscillation.

An example of measurement performed in this condition will be described. First, reference water such as pure water is injected to the quartz sensor 1. After frequency of the oscillator circuit 20 is stabilized, the sample solution is added. Then, difference between a frequency with the pure water and a frequency with the added sample is obtained. Thus, existence or concentration of the target substance in the sample is obtained based on a preliminarily formed calibration curve. This work may display a frequency detected by a frequency detector as a real-time graph through the user interface 4. Alternatively, the time-series data of frequency that is stored in the memory 44 of the main body 3 may be read out afterward.

Next, in the case where a quartz sensor is changed to a quartz sensor with the same frequency that has a different CI value in a liquid phase, a type of the quartz sensor is similarly changed through the user interface 4 by inputting the type information. This consequently switches the resistor for the voltage adjustment of the regulator 5 to, for example, the resistor R2. This in turn adjusts the drive voltage corresponding to the quartz sensor.

As described above, the sensing device according to this embodiment measures concentration of the target substance and determines existence or nonexistence of the target substance, based on change in natural frequency due to the target substance adsorbed by the piezoelectric resonator. The sensing device adjusts the DC drive voltage of the analog oscillator circuit 20 with respect to a plurality kinds of piezoelectric sensors (piezoelectric resonators) with mutually different CI values. This ensures an appropriate negative resistance. Accordingly, the analog oscillator circuit 20 is commonalized for piezoelectric resonators with mutually different CI values.

Second Embodiment

The voltage supply unit according to an embodiment disclosed here may employ a switching regulator. In this case, an ON/OFF duty ratio of a switching element that is used in the switching regulator corresponds to an output voltage (a feeding voltage to the oscillator circuit 20) of the switching regulator. Thus, the voltage data in the memory 44 is data where the type information of the quartz sensor 1 corresponds to data for setting the duty ratio. The switching regulator continuously changes its output voltage. This allows adding a new kind of the quartz sensor to be used by storing data indicative of the type and its duty ratio equivalent to a drive voltage that corresponds to the added quartz sensor in the memory 44.

Third Embodiment

Figure 5:
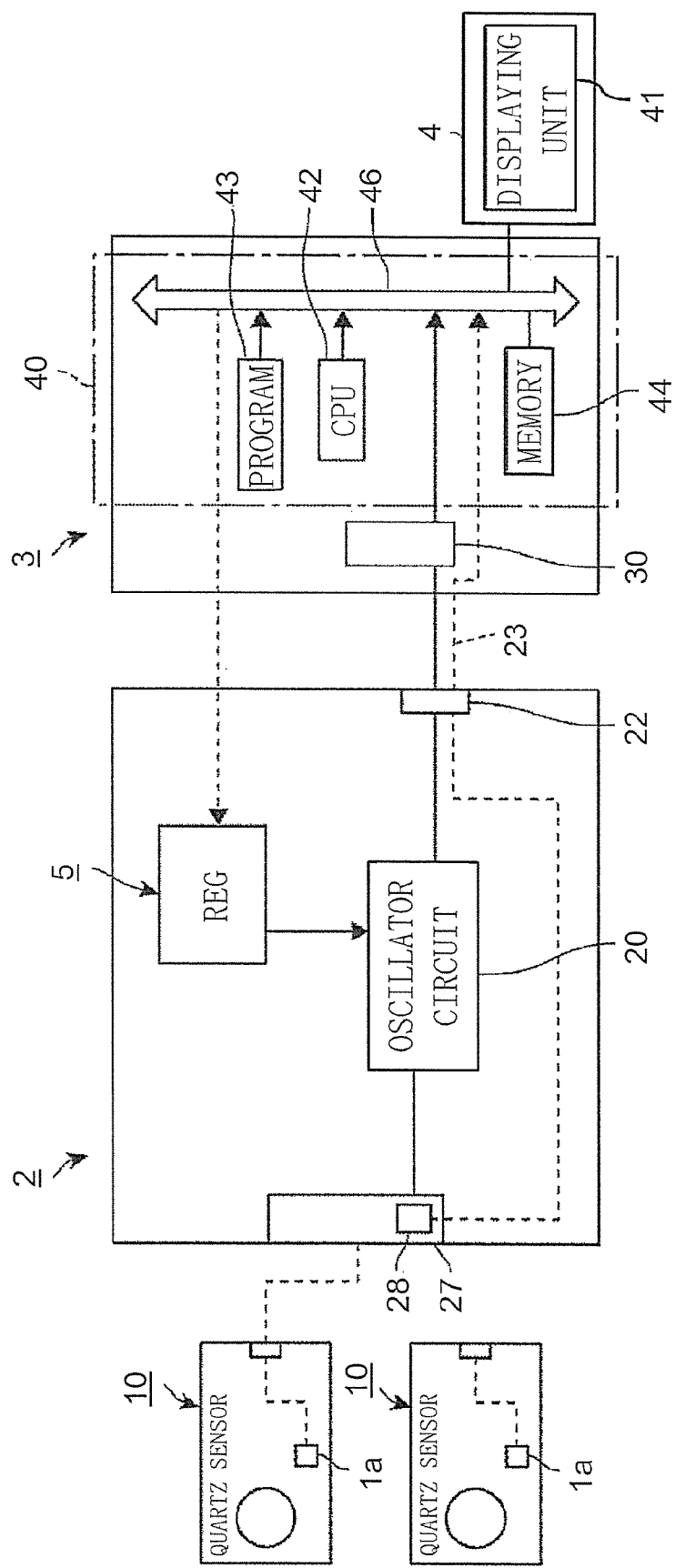
FIG. 5 is a block diagram illustrating a whole circuit of a sensing device according to a third embodiment disclosed here.

As illustrated in FIG. 5, a third embodiment is constituted such that the type information of the quartz sensor 10 to be used is input to the controller 40 from the quartz sensor 10 through the oscillator circuit unit 2 in the case where the quartz sensor 10 is connected to the oscillator circuit unit 2, instead of inputting the information by the operator through the user interface 4. The printed circuit board 60 (see FIG. 6A) of the quartz sensor 10 includes an IC chip 1a that includes a memory storing the type information while a signal path extends from the IC chip 1a in the printed circuit board 60. At an end portion of the signal path, a terminal 27 is disposed to be connected to a dedicated terminal 28 at the oscillator circuit unit 2 side when the quartz sensor 10 is inserted to the oscillator circuit unit 2. The cable 23, which connects the oscillator circuit unit 2 and the main body 3 together, includes a signal path to transmit data in the IC chip 1a of the quartz sensor 10 to the controller 40. Accordingly, when the quartz sensor 10 is connected to the oscillator circuit unit 2, type information of the quartz sensor 10 is transmitted to the controller 40 from the IC chip 1a. The controller 40 reads out data corresponding to the drive voltage of the oscillator circuit 20 corresponding to the type information, and then transmits a control signal to the voltage supply unit such as the regulator 5.

As described above, for example, the disclosure may have the oscillator circuit unit 2 that includes an operating unit for switching the switch 51 according to the first embodiment. This allows an operator to select a resistor (one of resistors R1 to R3) corresponding to a type of the quartz sensor to be used through the operating unit. In this case, the operating unit corresponds to a reading unit for the type information of the quartz sensor.

Figure 6:
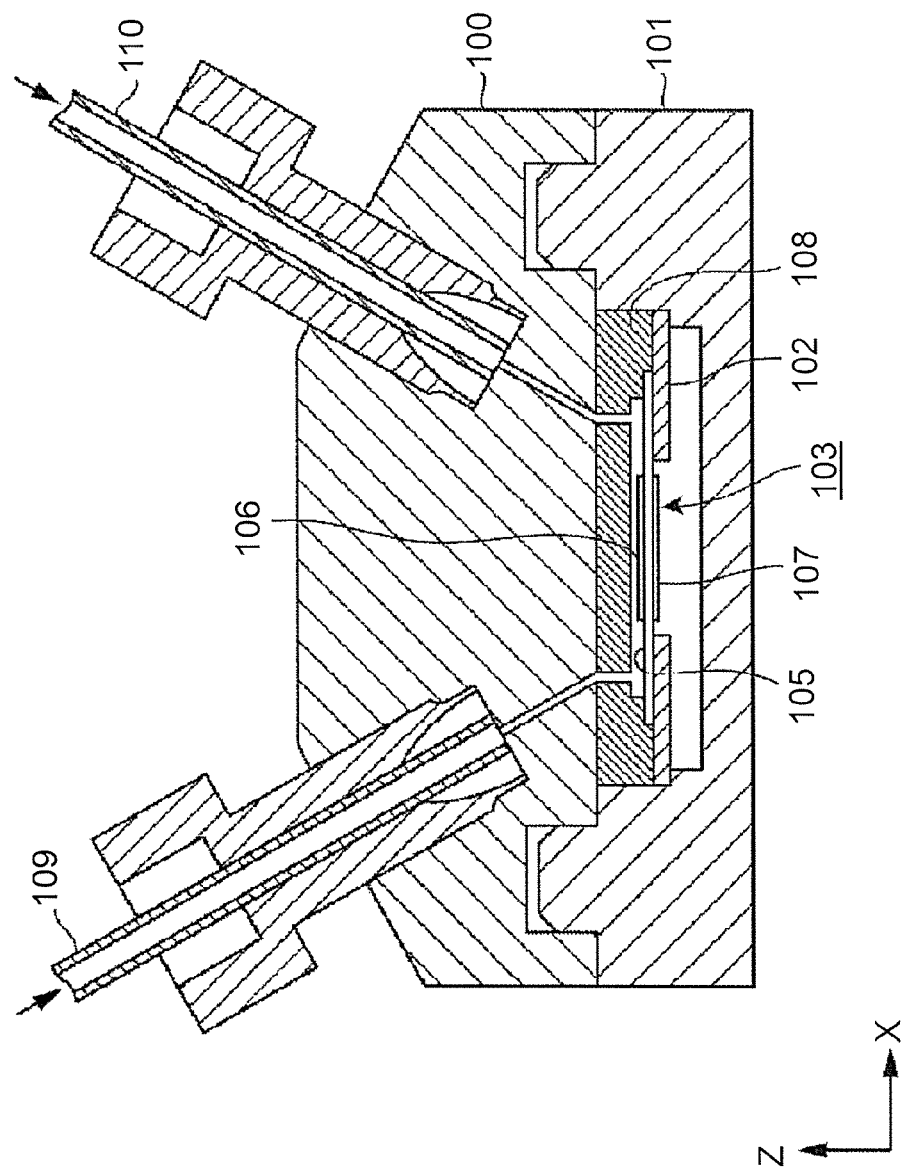
FIG. 6 is a longitudinal cross-sectional side view illustrating a whole configuration of a piezoelectric sensor according to another embodiment disclosed here.

While the sensing device according to an embodiment disclosed here is not limited to the sensing device using the piezoelectric sensor that accumulates the sample solution, the sensing device may be a sensing device that flows the sample solution, that is, flow-injection type piezoelectric sensor. FIG. 6 illustrates this kind of sensing device.

The sensing device in FIG. 6 includes an upper material 100, a lower material 101, a printed circuit board 102, a crystal unit 103, a crystal element 105, electrodes 106 and 107, a pressing member 108, a liquid supply port 109, and a liquid discharge port 110. The upper material 100 is removal from the lower material 101, thus allowing a replacement of the crystal unit 103. In the flow-injection type measuring unit, a sample solution flows to the liquid discharge port 110 side from the liquid supply port 109 via a space at a front surface side of the crystal unit 103. The measuring unit measures the oscillation frequency of the crystal unit 103 while flowing a reference solution or the sample solution. In this kind of sensing device, a height of the liquid flow space at the front surface side of the crystal unit 103 is changed depending on, for example, a kind of the target substance and a range of concentration to be measured. Sizes and shapes of the electrodes 106 and 107 in the crystal unit 103 may be changed corresponding to the changed height. In this case, this embodiment disclosed here ensures a communalized oscillator circuit, which brings an effective technique.

A known system includes two pairs of excitation electrodes in one crystal element. One pair of excitation electrodes includes an adsorbing layer that adsorbs a target substance is disposed while the other pair of excitation electrodes does not include any adsorbing layer. The system measures respective oscillation frequencies of the two pairs of excitation electrodes, thus estimating concentration of the target substance using the respective frequencies. While in a crystal vibration region of the other pair of electrodes, natural frequency is changed depending on temperature, the natural frequency is not changed depending on existence or nonexistence of the target substance. Accordingly, a value corresponding to frequency difference between crystal vibration regions of the respective pairs of electrodes is estimated. This estimation consequently reduces measurement error due to change in temperature. This disclosure is applicable to this crystal unit.

In the sensing device disclosed here, the voltage supply unit may include a regulator. The voltage adjusting unit may include a memory and a reading unit. The memory stores data of the type information of the piezoelectric resonator, for example a crystal unit, corresponds to information for adjustment of a regulator. The reading unit is configured to read out information corresponding to the type information of the crystal unit. The information is read out from the data in the memory.

This disclosure is also applicable to a sensing method for sensing a target substance in a sample fluid based on oscillation frequency of a piezoelectric resonator. The piezoelectric resonator includes a piezoelectric piece, an electrode disposed on the piezoelectric piece, and an adsorbing layer located on the electrode. The adsorbing layer adsorbs a target substance in the sample fluid. The piezoelectric resonator is configured to change a natural frequency of the piezoelectric resonator by adsorbing the target substance. The sensing method includes supplying, obtaining, and adjusting. The supplying supplies a DC drive voltage to an oscillator circuit. The oscillator circuit oscillates the piezoelectric resonator. The obtaining obtains type information of a piezoelectric resonator to be connected to the oscillator circuit. The adjusting adjusts the DC drive voltage to a voltage corresponding to a piezoelectric resonator to be used based on the type information obtained by the information obtaining unit.

This disclosure is applicable to the device that measures concentration of the target substance and determines existence or nonexistence of the target substance based on change in natural frequency due to the target substance that is adsorbed by the piezoelectric resonators. This disclosure adjusts a driving DC voltages of an analog oscillator circuits for a plurality kinds of piezoelectric sensors (piezoelectric resonators) with mutually different CI values so as to ensure their appropriate negative resistances in the device. Accordingly, this ensures the commonalized analog oscillator circuit for the piezoelectric resonators with mutually different CI values.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A sensing device to be connected to one of a plurality different kinds of piezoelectric resonators for sensing a target substance in a sample fluid based on oscillation frequency of the connected piezoelectric resonator, wherein
   the connected piezoelectric resonator comprising:
   a piezoelectric piece;
   an electrode disposed on the piezoelectric piece; and
   an adsorbing layer located on the electrode, the adsorbing layer adsorbing the target substance in the sample fluid, wherein
   the connected piezoelectric resonator is configured to change a natural frequency of the connected piezoelectric resonator by adsorbing the target substance, wherein
   the sensing device comprises:
   an oscillator circuit commonalized for the plurality different kinds of piezoelectric resonators having different crystal impedance values, and configured to be driven with voltages for the plurality different kinds of piezoelectric resonators, so that each of the corresponding voltages is corresponding to the crystal impedance value of the connected piezoelectric resonator, wherein the connected piezoelectric resonator is connected to the oscillator circuit;
   a voltage supply unit configured to supply a DC drive voltage to the oscillator circuit, so that the oscillator circuit is driven with the DC drive voltage corresponding to the crystal impedance value of the connected piezoelectric resonator;
   an information obtaining unit configured to obtain a type-information of the connected piezoelectric resonator; and
   a voltage adjusting unit configured to adjust the DC drive voltage to a voltage corresponding to the connected piezoelectric resonator based on the type-information obtained by the information obtaining unit.

2. The sensing device according to claim 1, wherein the voltage supply unit includes a regulator, wherein the voltage adjusting unit comprises:
   a memory that stores data of the type information of the piezoelectric resonator which corresponds to an information for adjustment of the regulator; and
   a reading unit configured to read out the information corresponding to the type information of the piezoelectric resonator, the information being read out from the data in the memory.

3. The sensing device according to claim 1, wherein the piezoelectric resonator comprises a crystal unit.

4. A sensing system for sensing a target substance in a sample fluid based on oscillation frequency of a piezoelectric resonator, the sensing system comprising:
   the sensing device according to claim 1; and
   the piezoelectric resonator.

5. A sensing system for sensing a target substance in a sample fluid based on oscillation frequency of a piezoelectric resonator, the sensing system comprising:
   the sensing device according to claim 2; and
   the piezoelectric resonator.

6. A sensing method for sensing a target substance in a sample fluid based on oscillation frequency of one of a plurality different kinds of piezoelectric resonators, wherein the one of the plurality different kinds of piezoelectric resonators comprising:

a piezoelectric piece;

an electrode disposed on the piezoelectric piece; and an adsorbing layer located on the electrode, the adsorbing layer adsorbing the target substance in the sample fluid, wherein the one of the plurality different kinds of piezoelectric resonators is configured to change a natural frequency of the one of the plurality different kinds of piezoelectric resonators by adsorbing the target substance, wherein the sensing method comprising:

supplying a DC drive voltage to an oscillator circuit, the oscillator circuit oscillating the one of the plurality different kinds of piezoelectric resonators, wherein the oscillator circuit is commonalized for the plurality different kinds of piezoelectric resonators having different crystal impedance values, and configured to be driven with voltages for the plurality different kinds of piezoelectric resonators, so that each of the voltages is corresponding to the crystal impedance value of one of the plurality of different kinds of piezoelectric resonators;

obtaining a type information of the piezoelectric resonator which is connected to the oscillator circuit; and adjusting the DC drive voltage to a voltage corresponding to a piezoelectric resonator to be used based on the type information obtained by the information obtaining unit, so that the oscillator circuit is driven with the DC drive voltage corresponding to the crystal impedance value of the one of the plurality of different kinds of piezoelectric resonators.

\* \* \* \* \*